(12) United States Patent
Liao

(10) Patent No.: US 9,370,503 B1
(45) Date of Patent: Jun. 21, 2016

(54) COMPOUNDS FOR TREATING OCULAR DISEASES

(71) Applicant: Chi Chou Liao, Taipei (TW)

(72) Inventor: Chi Chou Liao, Taipei (TW)

( * ) Notice: Subject to any disclaimer, the term of this patent is extended or adjusted under 35 U.S.C. 154(b) by 0 days.

(21) Appl. No.: 14/632,866

(22) Filed: Feb. 26, 2015

(51) Int. Cl.
*A61K 31/35* (2006.01)
*A61K 31/353* (2006.01)
*A61K 9/00* (2006.01)

(52) U.S. Cl.
CPC ............. *A61K 31/353* (2013.01); *A61K 9/0048* (2013.01)

(58) Field of Classification Search
CPC .................... A61K 31/353; A61K 9/0048
USPC ........................................ 514/456
See application file for complete search history.

(56) References Cited

U.S. PATENT DOCUMENTS

| 2006/0276458 A1* | 12/2006 | Chiou | A61K 31/55 514/223.5 |
| 2008/0139664 A1* | 6/2008 | Yeboah | A61K 31/00 514/646 |

FOREIGN PATENT DOCUMENTS

JP          2010195762     * 9/2010

* cited by examiner

*Primary Examiner* — T. Victor Oh
(74) *Attorney, Agent, or Firm* — Birch, Stewart, Kolasch & Birch, LLP.

(57) ABSTRACT

The present invention provides a method for treating an ocular disease in a subject in need thereof, comprising administering an effective amount of a compound of Formula (A) to the subject. Also provided is a pharmaceutical composition for treating an ocular disease, which comprises compound of Formula (A), and a pharmaceutically acceptable carrier.

7 Claims, 13 Drawing Sheets

Compound of Formula (II) (μg/ml)

Compound of Formula (II) (μg/ml)

Compound of Formula (II) (µg/ml)

Compound of Formula (II) (µg/ml)

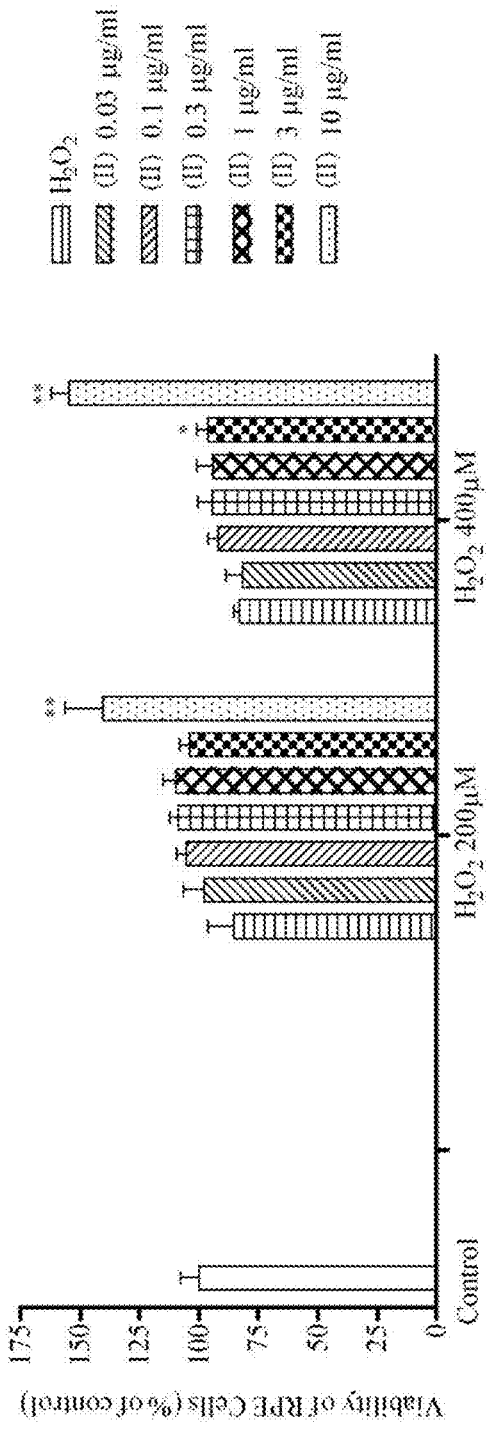
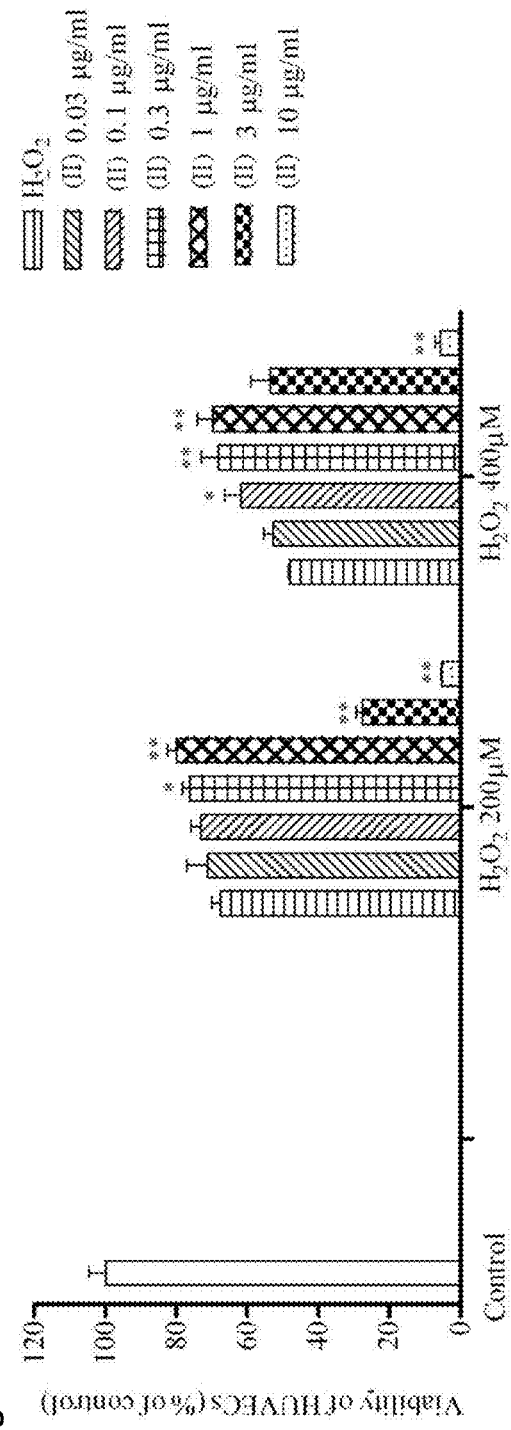
Fig. 4A
Fig. 4B

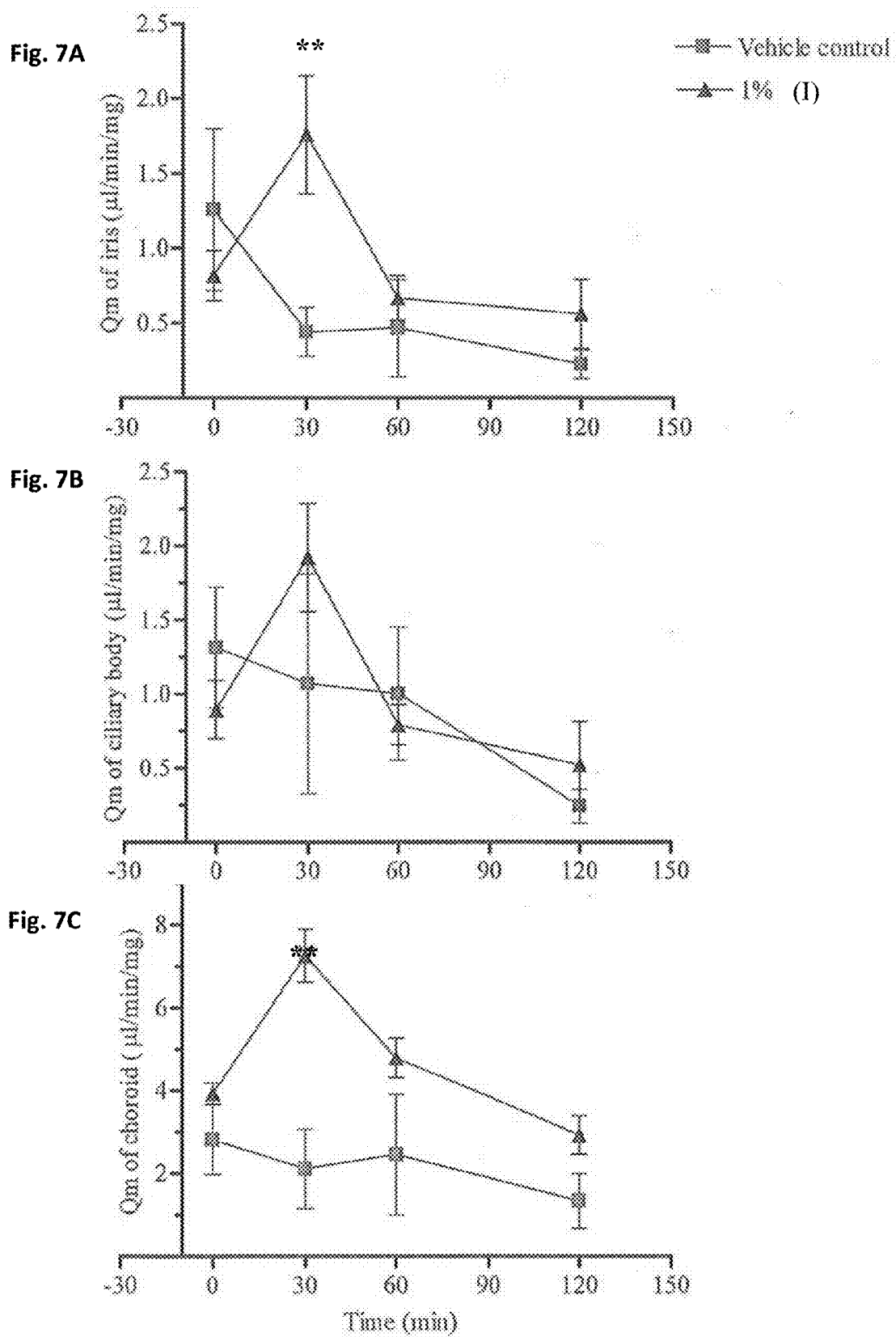

COMPOUNDS FOR TREATING OCULAR DISEASES

FIELD OF THE INVENTION

The present invention pertains to a method for treating an ocular disease.

BACKGROUND OF THE INVENTION

As the population grows older and older, the deterioration of visual functions becomes more and more apparent and serious. There are numerous eye diseases which are closely related to aging, such as glaucoma, age-related macular degeneration (AMD), optic neuropathy, ischemic retinopathy, senile cataract, and the like. These eye diseases are the major ones which cause visual disturbance or even blindness of the elderly.

The retinal pigment epithelium (RPE) is composed of monolayer of cells and located between the retinal photoreceptors and the choroidal blood vessels which plays a key role in the mechanical and metabolic support of the photoreceptors. In addition, dysfunctioned RPE is the main cause of some ocular diseases, such as proliferative vitreoretinopathy (PVR), uveitis and AMD. AMD and other diseases, such as diabetic retinopathy (DR), are probably linked to the effects of oxygen radicals derived from light or metabolic reactions.

On the other hand, ocular blood flow is also closely related to numerous eye diseases, including glaucoma, ischemic retinopathy, and age-related macular degeneration (AMD). Thus, maintenance of normal ocular blood flow is essential to prevent/treat the aforementioned eye diseases.

Age-related macular degeneration (AMD) is the leading cause of blindness in people over the age of 65 in the United States and Western Europe. Risk factors common to both continents include increasing age, cigarette smoking, hypertension, angina and a positive family history. AMD exists in both non-exudative and exudative forms. The non-exudative form involves atrophy of the central retina with a slow and progressive loss of central vision. The exudative form is characterized by the growth of new blood vessels through Bruch's membrane into the subretinal space, and the development of choroidal neovascularization (CNV) through an angiogenic process. Angiogenesis is often triggered by ischemia and hypoxia. As the macula has only a single blood supply, and the retina has the highest uptake of oxygen in the body, it is not surprising to observe that ischemia is strongly associated with AMD development (Strauss O., Physiol. Res. 2005; 85(3):845-881).

Since the epithelium is very vulnerable to changes in oxygen tensions and oxygen radical-linked stress, reactive oxygen species (ROS) produced in the RPE during ischemia-linked diseases may be injurious to RPE cells. An important "early" event of AMD is the loss of RPE cells due to oxidative damage. Oxidative stress has been recognized to be involved in the etiology of several age-related chronic diseases, such as cancer, diabetes, neurodegenerative and cardiovascular diseases.

BRIEF SUMMARY OF THE INVENTION

It is unexpectedly found in the present invention that a prenylflavanone compound having a general Formula (A) is effective in treating ocular diseases:

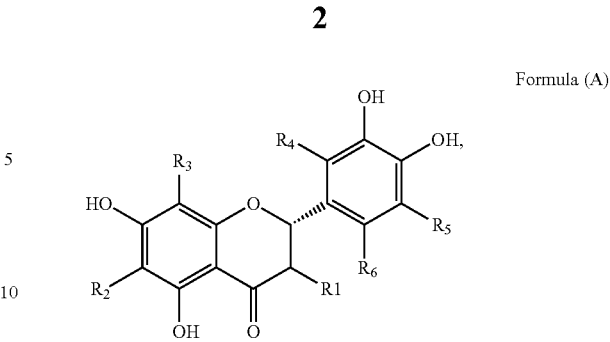

Formula (A)

wherein $R_1$, $R_2$, $R_3$, $R_4$, $R_5$, and $R_6$ independently, represent —H, —OH, a linear or branched alkyl group, or an isoprene group substituted or non-substituted with —OH.

Accordingly, in one aspect, the present invention features a method for treating an ocular disease in a subject in need thereof, comprising administering an effective amount of a compound of Formula (A) to the subject.

In another aspect, the present invention provides a pharmaceutical composition for treating an ocular disease comprising a compound of Formula (A), and a pharmaceutically acceptable carrier.

The compound of Formula (A) is chemically synthesized through a process known in the art.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings:

FIG. 4A shows the effect of (II) on $H_2O_2$-induced injury in ARPE-19 cells. ARPE-19 cells were incubated with (II) and $H_2O_2$ for 24 hours. FIG. 4B shows the effect of (II) on $H_2O_2$- induced injury in HUVECs. HUVECs were incubated with (II) and H$_2$O$_2$ for 24 hours. Data are expressed as means±SEM. n=6 in each group; *P<0.05 and **P<0.01 vs. model group.

Figure 5A:
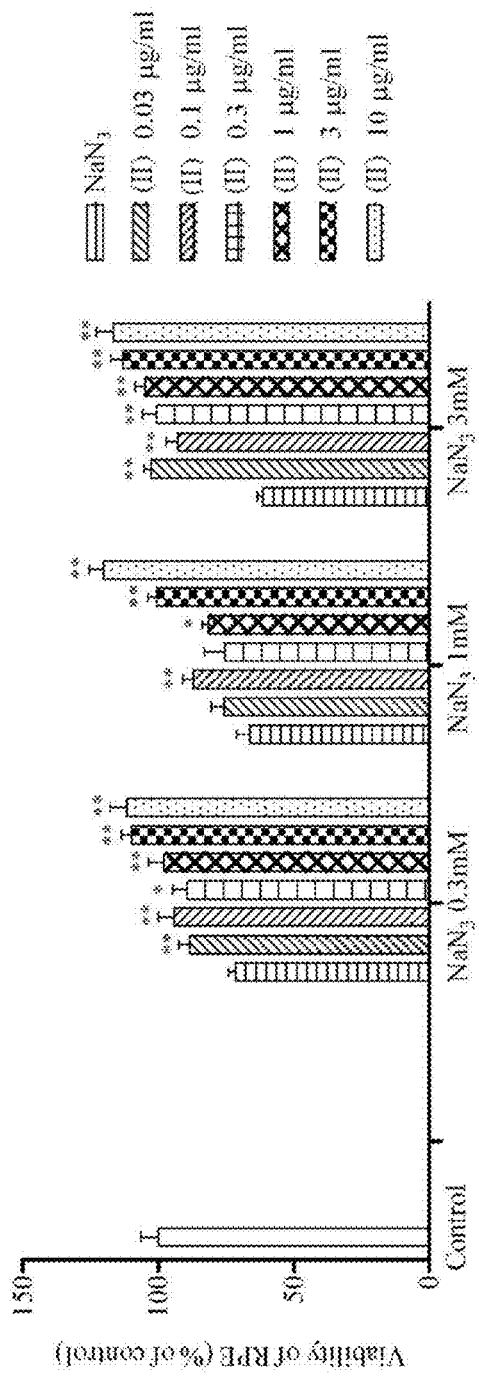
Figure 5B:
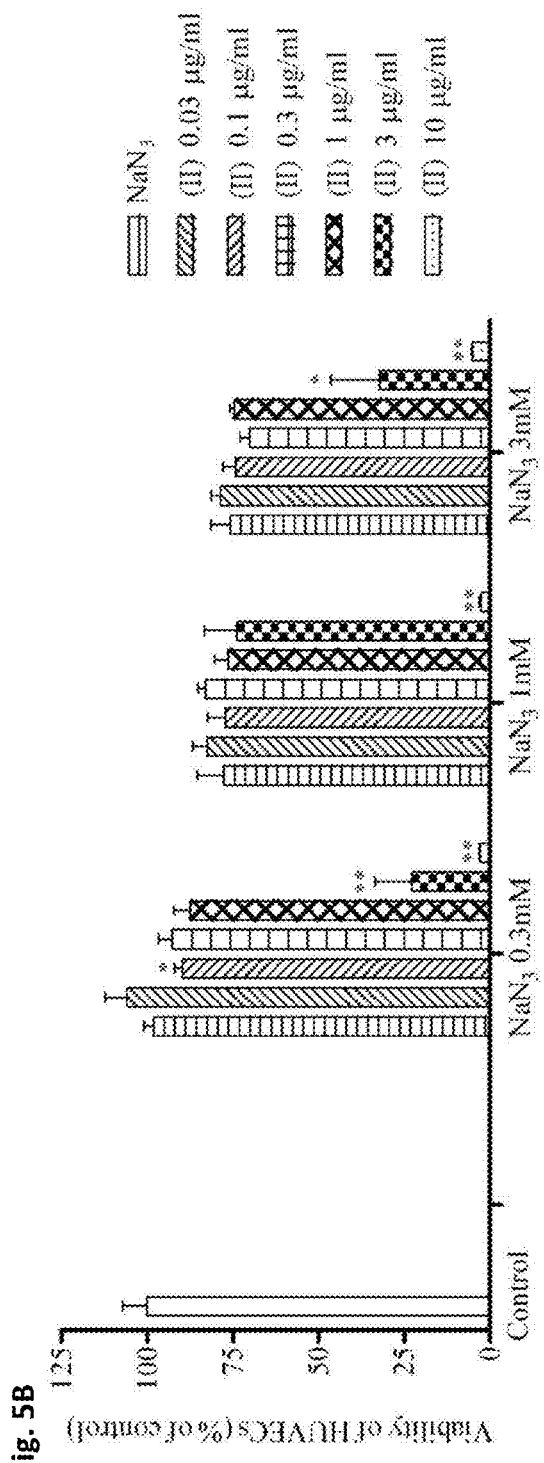

FIG. 5A shows the effect of (II) on NaN$_3$-induced injury in ARPE-19 cells. ARPE-19 cells were incubated with (H) and NaN$_3$ for 72 hours. FIG. 5B shows the effect of (II) on NaN$_3$-induced injury in HUVECs. HUVECs were incubated with (II) and NaN$_3$ for 72 hours. Data were expressed as means±SEM. n=6 in each group; *P<0.05 and **P<0.01 vs. model group.

Figure 6A:
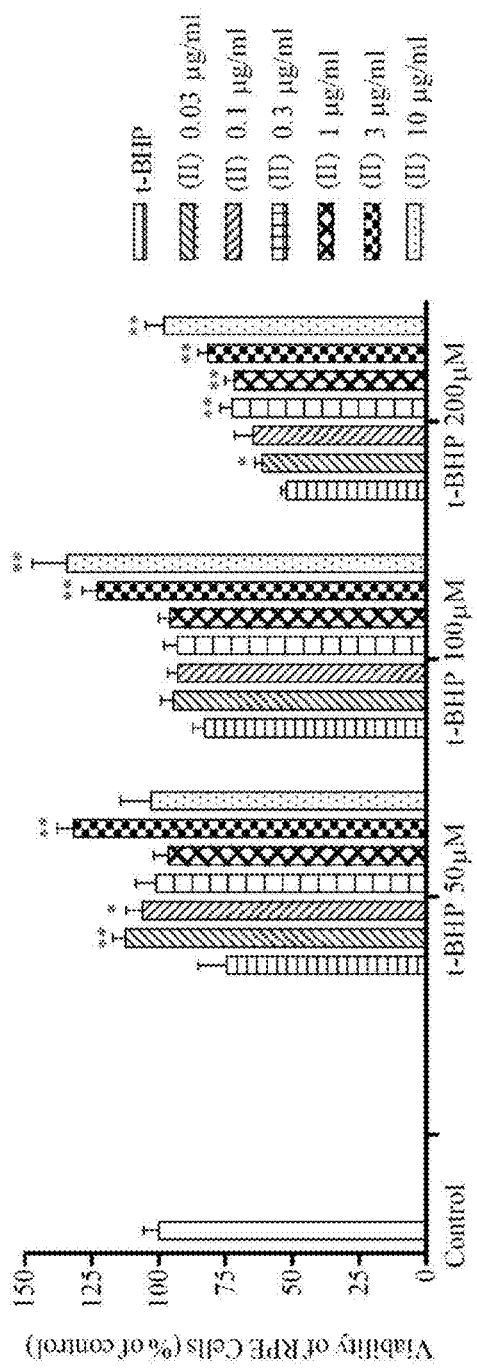
Figure 6B:
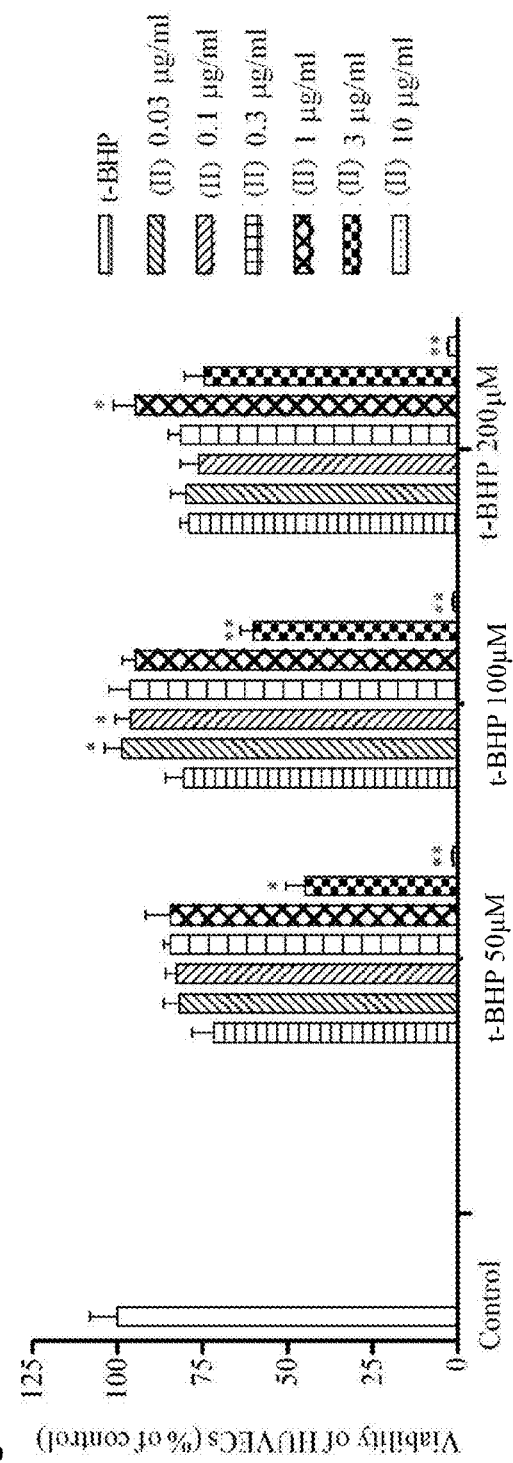

FIG. 6A shows the effect of (II) on t-BHP-induced injury in ARPE-19 cells. ARPE-19 cells were incubated with (II) and t-BHP for 12 hours. FIG. 6B shows the effect of (II) on t-BHP-induced injury in HUVECs. HUVECs were incubated with (II) and t-BHP for 12 hours. Data are expressed as means±SEM. n=6 in each group; *P<0.05 and **P<0.01 vs. model group.

FIGS. 7A-7C show the effects of 1% compound of Formula (I) ("(I)") on Ocular Blood Flow in Ocular Hypertensive Rabbit, wherein FIG. 7A shows the blood flow of iris in Qm; FIG. 7B shows the blood flow of ciliary body in Qm; and FIG. 7C shows the blood flow of choroid in Qm.

Figure 8A:
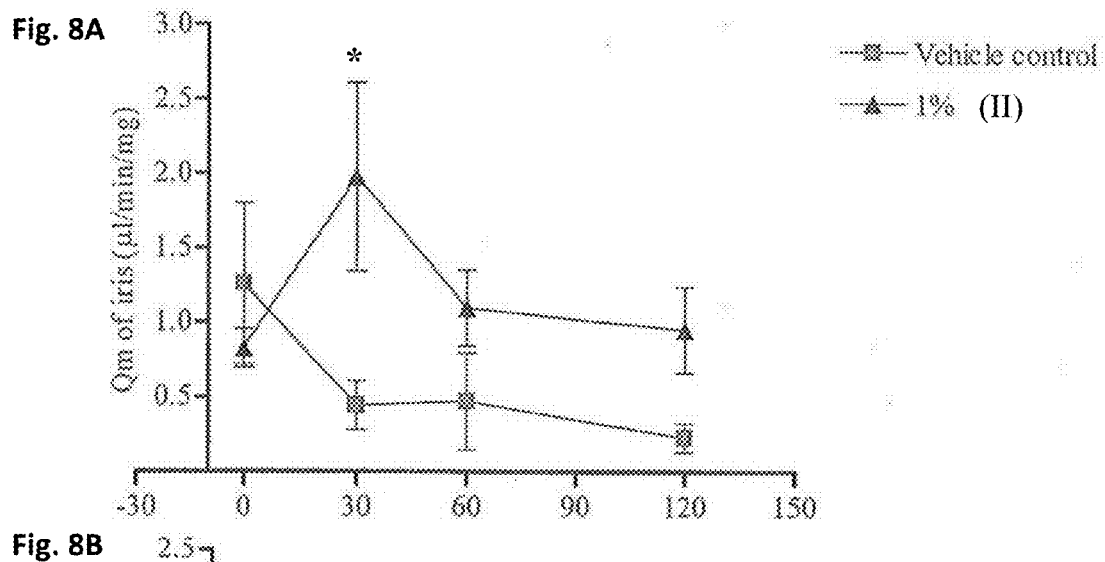
Figure 8B:
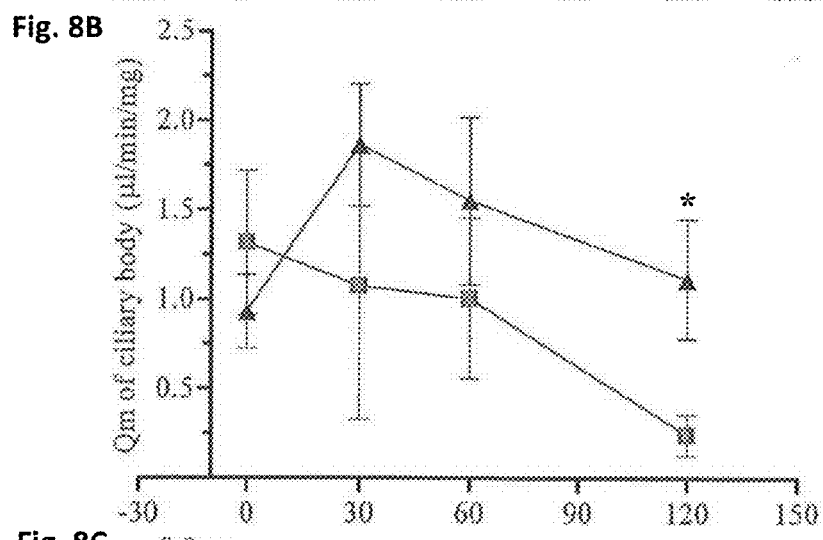
Figure 8C:
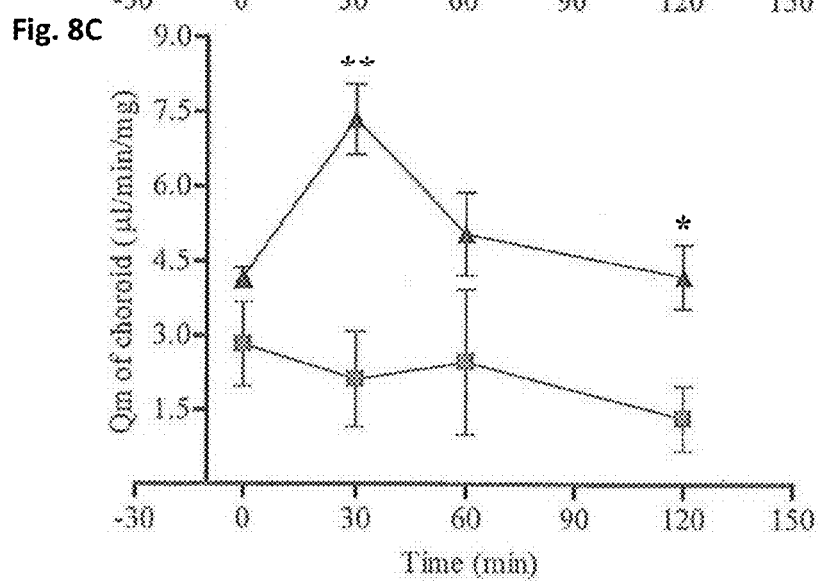

FIGS. 8A-8C show the effects of 1% (II) on Ocular Blood Flow in Ocular Hypertensive Rabbit, wherein FIG. 8A shows the blood flow of iris in Qm; FIG. 8B shows the blood flow of ciliary body in Qm; and FIG. 8C shows the blood flow of choroid in Qm.

Figure 9:
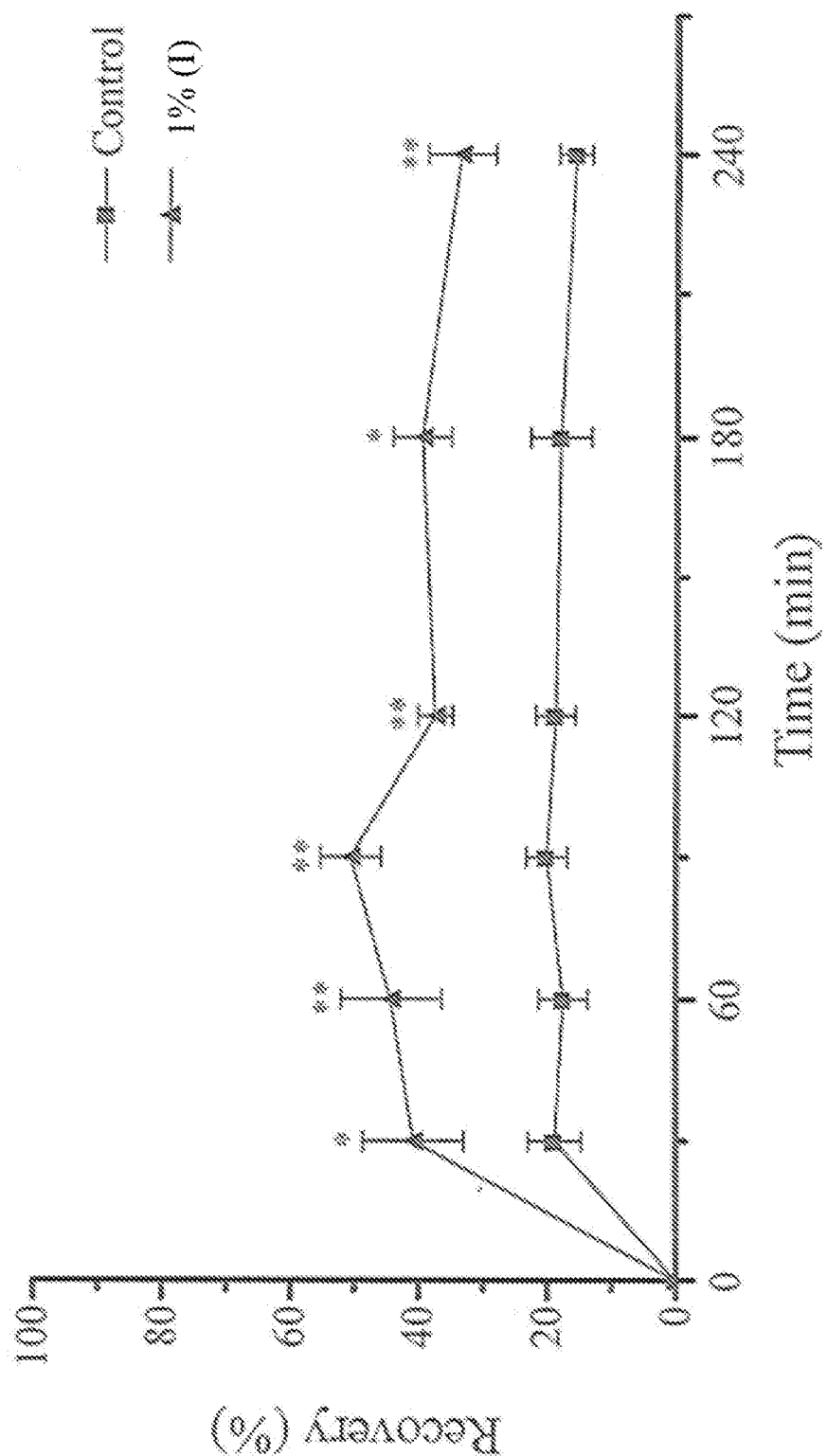

FIG. 9 shows the effect of (I) on b-wave recovery of rat's retinal function after ischemic insult. Stars represent significant difference between control and the treated at P<0.05 (*) and P<0.01 (**).

Figure 10:
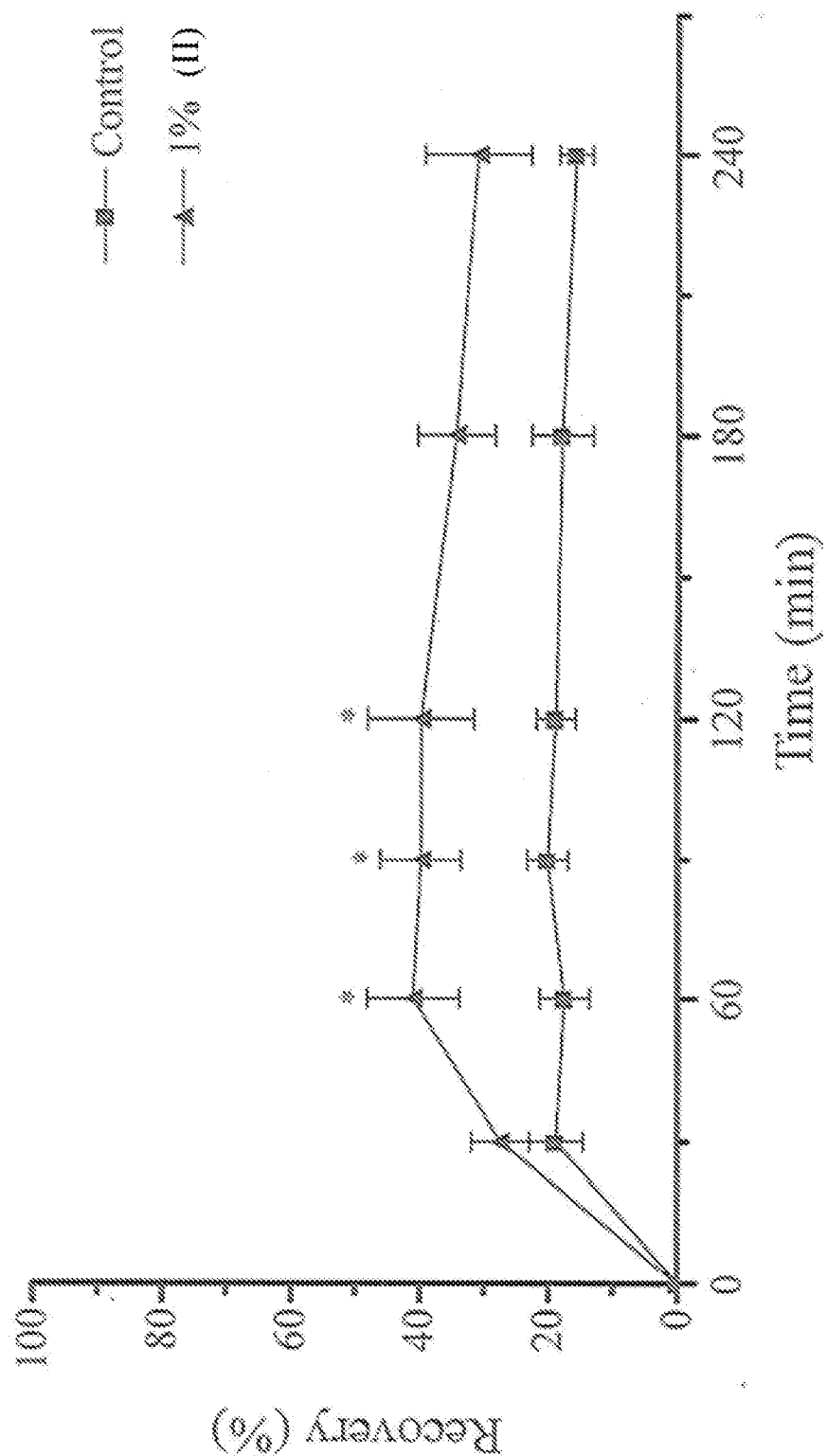

FIG. 10 shows the effect of (II) on b-wave recovery of rat's retinal function after ischemic insult. Stars represent significant difference between control and the treated at P<0.05 (*).

Figure 11:
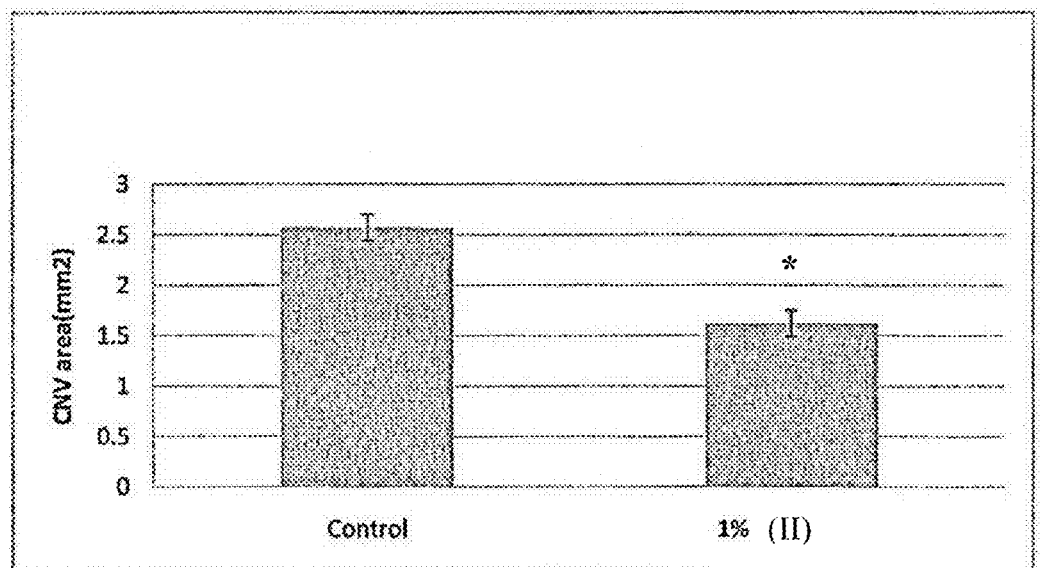

FIG. 11 shows the effects of 1% (II) on laser induced AMD rat model. Star represents significant difference between two values at P<0.05.

Figure 12:
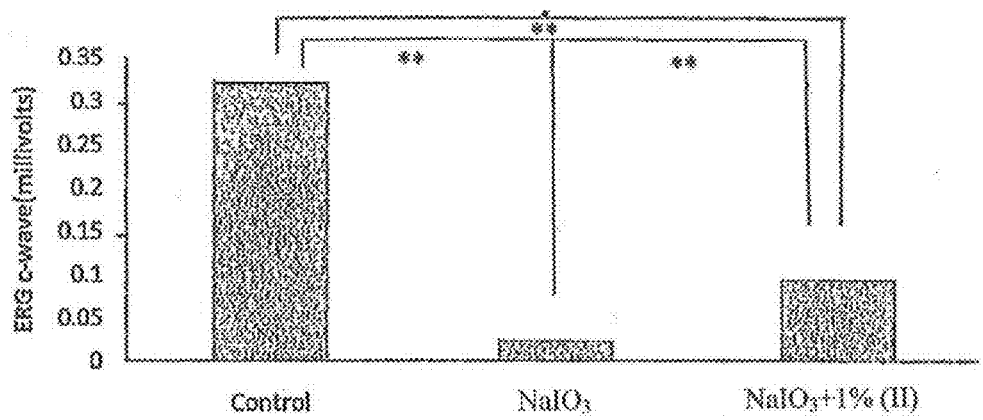

FIG. 12 shows the effects of 1% (II) on NaIO$_3$ induced dry AMD rat model. Stars represent significant difference between two values at P<0.01.

Figure 13:
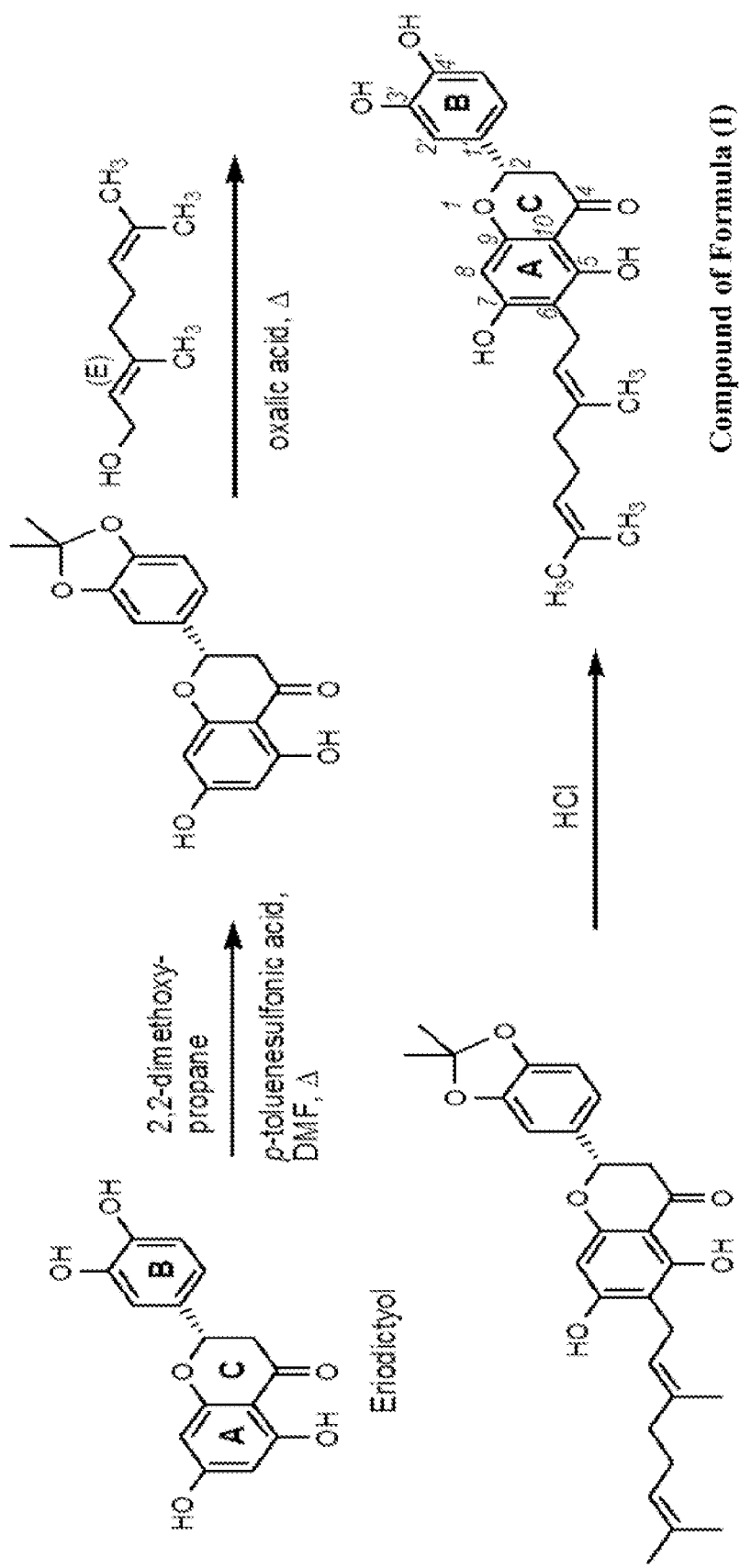

FIG. 13 shows a scheme for synthesizing a compound of Formula (I).

Figure 14:
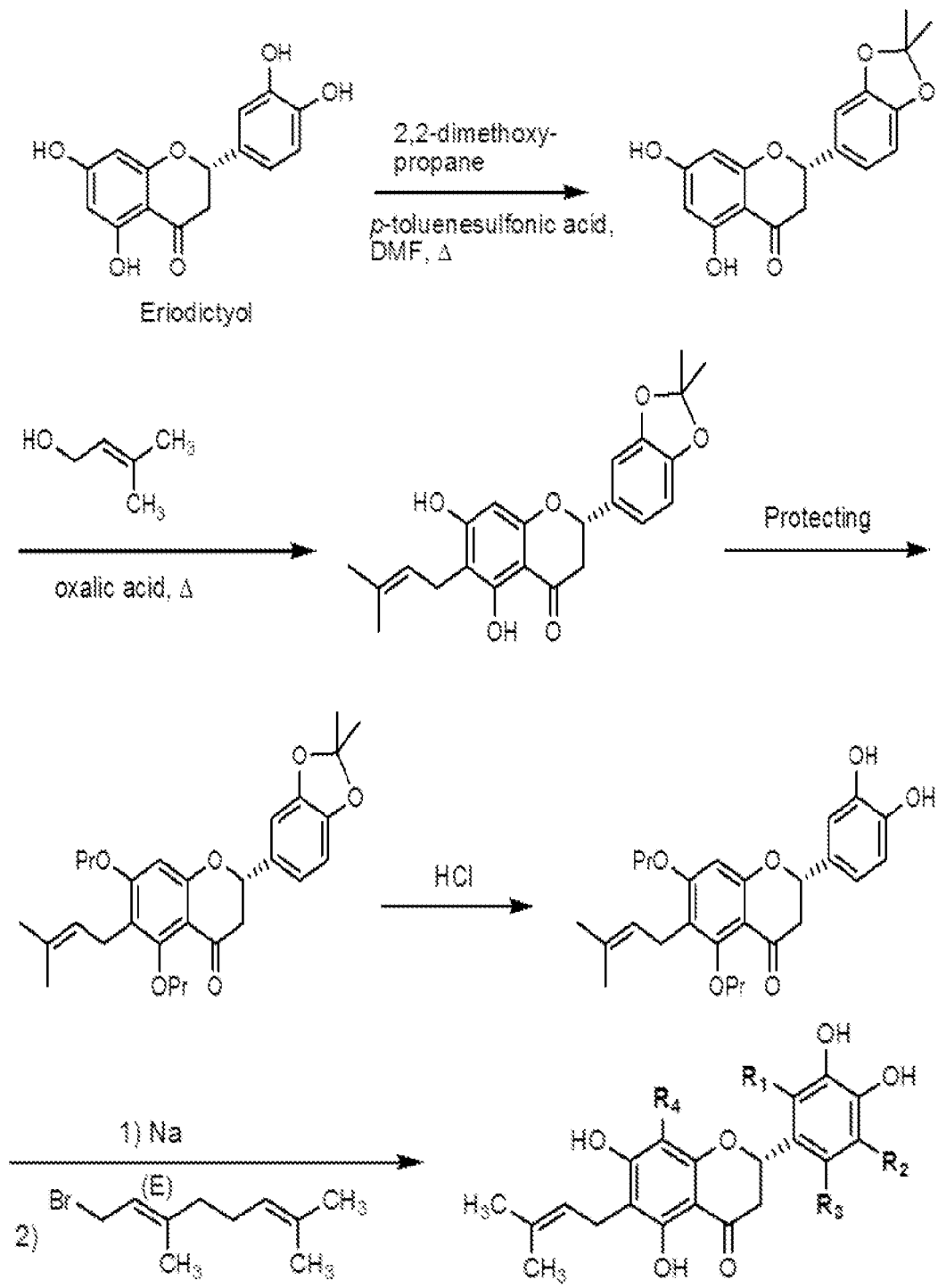

FIG. 14 shows a scheme for synthesizing a compound of Formula (II).

DETAILED DESCRIPTION OF THE INVENTION

In one aspect, the present invention features a method for treating an ocular disease in a subject in need thereof, comprising administering an effective amount of a compound of Formula (A) to the subject:

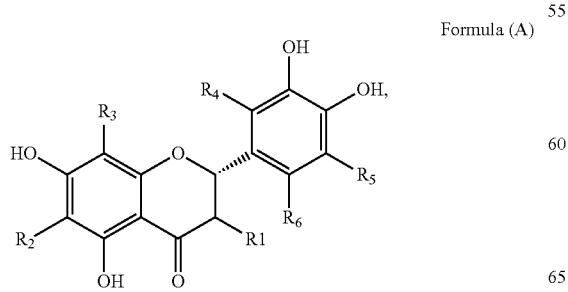

Formula (A)

wherein $R_1$, $R_2$, $R_3$, $R_4$, $R_5$, $R_6$, $R_7$ independently represent —H, —OH, a linear or branched alkyl group, or an isoprene group substituted or non-substituted with —OH. Some examples of a compound of Formula (A) can be found in U.S. Pat. No. 7,585,892, which are incorporated by reference in its entirety.

The compound of Formula (A) is chemically synthesized through a process known in the art.

For example, a compound of Formula (I) may be synthesized through Scheme I as shown in FIG. 13:

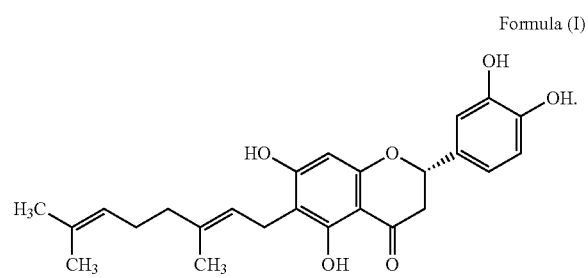 [SMILES: CC(C)=CCC/C(C)=C/Cc1c(O)cc2c(c1O)C(=O)C[C@@H](c1ccc(O)c(O)c1)O2]

Formula (I)

In another example, a compound of Formula (II) may be synthesized through Scheme II as shown in FIG. 14:

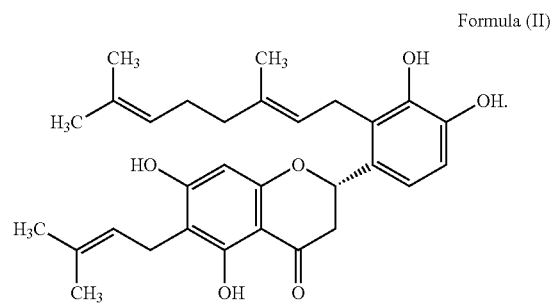 [SMILES: CC(C)=CCC/C(C)=C/Cc1c([C@@H]2CC(=O)c3c(cc(O)c(CC=C(C)C)c3O)O2)ccc(O)c1O]

Formula (II)

A compound of Formula (A) used in the present invention includes but is not limited to a compound having any of the structures of Formulae I to X:

Formula (I)

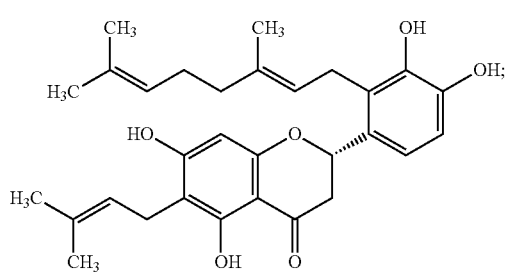
Formula (II)
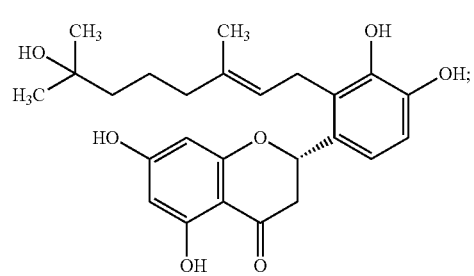
Formula (III)
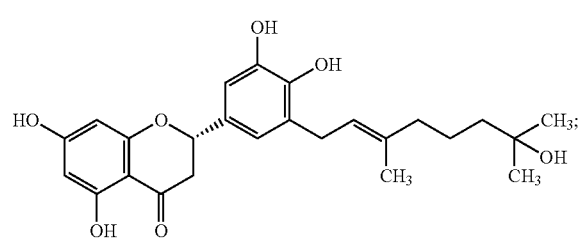
Formula (IV)
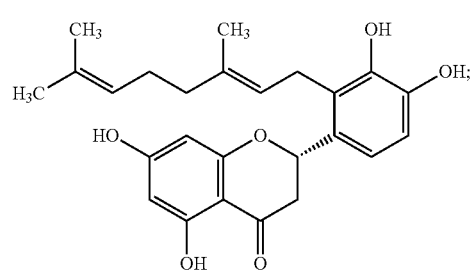
Formula (V)
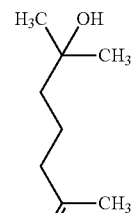
Formula (VI)
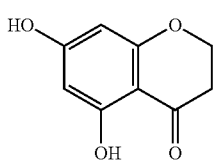
Formula (VII)
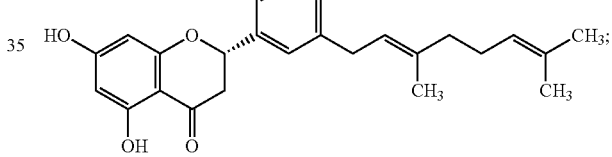
Formula (VIII)
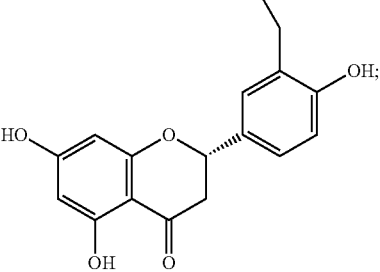

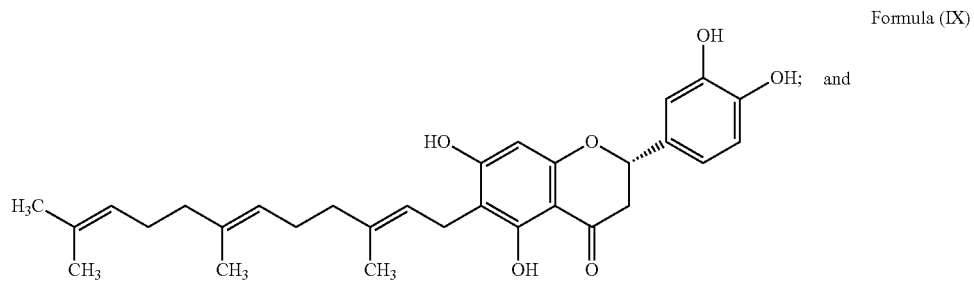 [SMILES: CC(C)=CCC/C(C)=C/CC/C(C)=C/Cc1c(O)cc2c(c1O)C(=O)C[C@@H](c1ccc(O)c(O)c1)O2 ; "and"]

Formula (IX)

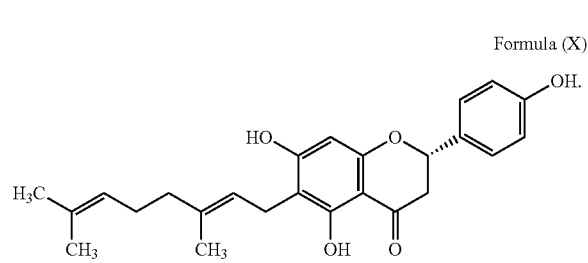 [SMILES: CC(C)=CCC/C(C)=C/Cc1c(O)cc2c(c1O)C(=O)C[C@@H](c1ccc(O)cc1)O2]

Formula (X)

The term "ocular disease" as used herein refers to a disease in association with eyes, including but not limited to glaucoma, age-related macular degeneration (AMD), ischemic retinopathy, optic neuropathy, diabetic retinopathy (DR), diabetic macular edema (DME), uveitis, and senile cataract. The ocular disease may be a disease or disorder associated with oxidative stress and/or hypoxia-induced damages to the eyes, or more particularly to the retinal pigment epithelium (RPE), including but not limited to glaucoma, AMD, ischemic retinopathy, optic neuropathy, DR and DME. The ocular disease may be a disease or disorder associated with reduced ocular blood flow, including but not limited to glaucoma, ischemic retinopathy, DR and AMD.

The term "effective amount" as used herein refers to a sufficient amount of a compound of Formula (A) to provide desired therapeutic effects, or the induction of a particular type of response. The effective amount required varies from subject to subject, depending on the disease state, physical conditions, age, sex, species and weight of the subject, etc. However, an appropriate effective amount can be determined by one of ordinary skill in the art using only routine experimentation. In one embodiment of the present invention, the effective amount is an amount effective to enhance the viability of RPE cells suffer from oxidative stress and/or hypoxia-induced damages. In one preferred embodiment, the effective amount is an amount effective to enhance the viability of RPE cells suffer from oxidative stress and/or hypoxia-induced damages, and in the same time having little or no effect on the viability of human umbilical vein endothelial cells (HUVECs) or effective to decrease the viability of HUVECs. In another embodiment of the present invention, the effective amount is an amount effective to enhance ocular blood flow. In one further embodiment, the effective amount is an amount effective to reduce choroidal neovascularization (CNV). In another embodiment, the effective amount is an amount effective to enhance RPE function at least by enhancing or recovering its c-wave amplitude as measured by ERG. For example, the compound of Formula (A) may be administered orally to a subject 1-3 times a day. For each oral administration, the amount of compound of Formula (A) may be 0.5 to 50 mg, preferably 2-25 mg. The compound of Formula (A) may also be administered to a subject through ophthalmological administration, 1-10 applications at a time, 1-10 times daily, preferably 1-5 applications at a time, 1-4 times daily. For example, one may use 3 drops of a preparation comprising the compound of Formula (A) each time, 3 times daily. For topical ophthalmological administrations, 0.01-10% compound of Formula (A) may be used, preferably, 0.1-1.0% compound of Formula (A) may be used.

In the examples of the invention, it is evidenced that compounds of Formula (A) were effective in treatment in various ocular diseases, such as retinal dysfunction after ischemic insult, and laser induced AMD.

Accordingly, a compound of Formula (A) may be administered to a subject suffering from an ocular disease, wherein the ocular disease is selected from the group consisting of glaucoma, age-related macular degeneration (AMD), ischemic retinopathy, optic neuropathy, diabetic retinopathy, diabetic macular edema, uveitis, and senile cataract. In one example of the invention, the ocular disease is AMD. In one specific embodiment, the ocular disease is dry AMD. The ocular disease may be or may not be an eye cancer.

In another aspect, the present invention provides a pharmaceutical composition for treating an ocular disease comprising a compound of Formula (A), and a pharmaceutically acceptable carrier The pharmaceutical composition of the present invention can be manufactured by conventionally known methods with one or more pharmaceutically acceptable carriers. The term "pharmaceutically acceptable carrier" as used herein encompasses any of the standard pharmaceutical carriers. Such carriers may include, but are not limited to: saline, buffered saline, dextrose, water, glycerol, ethanol, propylene glycol, cremophor, nanoparticles, liposome, polymer, and combinations thereof.

The pharmaceutical composition of the present invention may be constituted into any form suitable for the mode of administration selected. For example, compositions suitable for oral administration include solid forms, such as pills, capsules, granules, tablets, and powders, and liquid forms, such as solutions, syrups, elixirs, and suspensions. Forms useful for topical administration include cream, ointment, gel, suspension, drops, emulsions, skin patches.

In addition to standard carriers, an oral pharmaceutical composition of the present invention may be supplemented with one or more excipients that are normally employed in oral formulations, such as surfactants, inhalants, solubilizers, stabilizers, emulsifiers, thickeners, coloring agents, sweetening agents, flavoring agents, and preservatives. Such excipients are well known to those skilled in the art.

According to the invention, the pharmaceutical composition may be administered to a subject through any route, such as oral administration, parenteral injection, eye injection (e.g., intravitreal injection), skin patch, or topical administration on the eyes. The pharmaceutical compositions for topical administration may be formulated in the form of eye ointment, eye gel, eye cream, or eye drop.

In one preferred embodiment, the pharmaceutical composition comprises a compound of Formula (I):

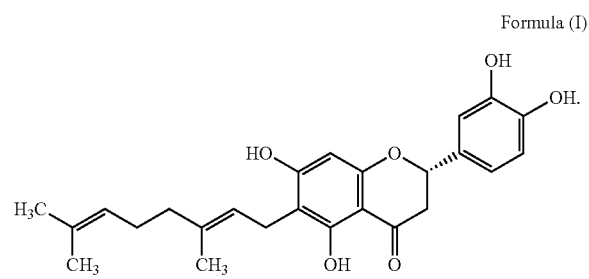 [SMILES: CC(C)=CCC/C(C)=C/Cc1c(O)cc2c(c1O)C(=O)C[C@@H](c1ccc(O)c(O)c1)O2]

Formula (I)

In another preferred embodiment, the pharmaceutical composition comprises a compound of Formula (II):

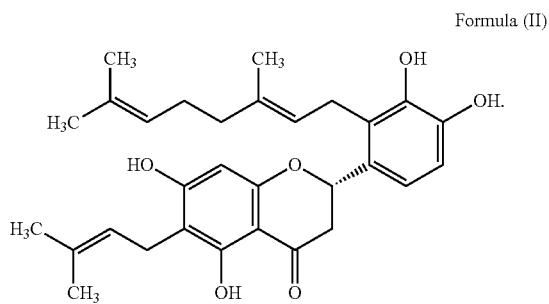 [SMILES: CC(C)=CCC/C(C)=C/Cc1c([C@@H]2CC(=O)c3c(cc(O)c(CC=C(C)C)c3O)O2)ccc(O)c1O]

Formula (II)

The present invention is further illustrated by the following examples, which are provided for the purpose of demonstration rather than limitation.

EXAMPLES

Example 1

Synthesis of a Compound of Formula (A)

A compound of Formula (I) was synthesized following Scheme I as set forth in FIG. 13. A compound of Formula (II) was synthesized following Scheme II as set forth in FIG. 14. Using Scheme II, a compound of Formula (B) as shown in FIG. 14 may be synthesized, wherein R1, R2, R3 and R4 are independently selected from the group consisting of a hydrogen group (H) and a geranyl group.

Example 2

Effect of a Compound of Formula (II) on Oxidation-Induced Injury in ARPE-19 Cells and HUVECs Materials and Methods
1. Materials Thiazolyl blue tetrazolium bromide (MTT, purity≥97.5%), Dulbecco's phosphate buffered saline (DPBS), hydrogen peroxide ($H_2O_2$, 50 wt. % solution in water), tert-butyl hydroperoxide (t-BHP, 70 wt. % in water), sodium iodate ($NaIO_3$, purity≥99.5%), sodium azide ($NaN_3$, purity≥99.5%) and Dulbecco's modified Eagle's medium/Ham's F12 (DMEM /F12, 1:1) were all purchased from Sigma-Aldrich Chemical Co. (St. Louis, Mo., USA). Human retinal pigment epithelium (ARPE-19) cells, human umbilical vein endothelial cells (HUVECs), fetal bovine serum (FBS), vascular cell basal medium and endothelial cell growth kit were purchased from ATCC (Manassas, Va., USA).

Human retinal pigment epithelium (RPE) cells are critical/unique cells located between photocells and choroid layer to provide nutrients to photocells as well as to remove metabolic wastes away from photocells in order to maintain normal/good visual function/activity. On the other hand, HUVECs are located on the vasculatures all over the body, including choroidal and retinal vessels. They are particularly had to the visual function via choroidal neovascularization. Suppression of neovascularization with VEGF inhibitors is the major mechanism to reduce angiogenesis/neovascularization for the treatment of wet AMD. Therefore, drugs that can increase the cell proliferation/growth of RPE but have no effect or suppress the cell growth of HUVEC would be useful in preventing/treating AMD.

2. Cell Culture

ARPE-19 cells were grown in DMEM/F12 medium supplemented with 10% FBS, 100 units/ml penicillin G, and 100 μg/ml streptomycin sulfate. HUVECs were grown in vascular cell basal medium supplemented with endothelial cell growth kit. Cells were incubated in a humidified incubator at 37° C. under 5% $CO_2$ and 95% air.

3. Effect of Compound of Formula (II) on the Viability of ARPE-19 Cells and HUVECs MTT assay was used to measure the viability of ARPE-19 cells and HUVECs. $2 \times 10^5$ ARPE-19 cells or $5 \times 10^4$ HUVECs were seeded in 96-well plates (100 μl/well) and allowed to grow overnight. Negative control was prepared by adding 100 μl medium without cells. The cells were then treated with fresh medium with a compound of Formula (II) ("(II)") (0.03, 0.1, 0.3, 1, 3 and 10 μg/ml) and/or oxidants ($NaIO_3$, $H_2O_2$, t-BHP and $NaN_3$) for 12, 24, or 72 hours (200 μl/well). The vehicle control group was treated with vehicle. 20 μl MTT (5 mg/ml) was added to wells, and incubated for another 4 h. After incubation, the medium was discarded and 100 μl DMSO was added to solubilize formazan produced from MTT by the viable cells. Absorbance was measured at 570 nm using a microplate reader (Bio-Rad Laboratories, Inc., CA). Cells viability was calculated according to the following formula: Viability of cells (%)=(absorbance in tested sample−absorbance in negative control)/(absorbance in vehicle control−absorbance in negative control)×100%.

4. Hypoxia Treatment

Cells were allowed to attach overnight, and then exposed to (II) or vehicle under hypoxic condition for 72 h. Hypoxic conditions (1% $O_2$, 5% $CO_2$ and 94% $N_2$) were maintained by using a temperature and humidity controlled environmental C-chamber by $O_2$ and $CO_2$ controllers (Proox Model 110 and Pro $CO_2$ Model 120, Bio Spherix Ltd., Redfield, N.Y., USA) with $N_2$ and $CO_2$ gas sources.

5. Statistical Analysis

All data were expressed as means S.E.M. Statistical analysis was performed using the Student's t-test. A value of P<0.05 was considered to be statistically significant.

Results

1. Cytotoxicity of (II) in ARPE-19 Cells and HUVECs

Figure 1A:
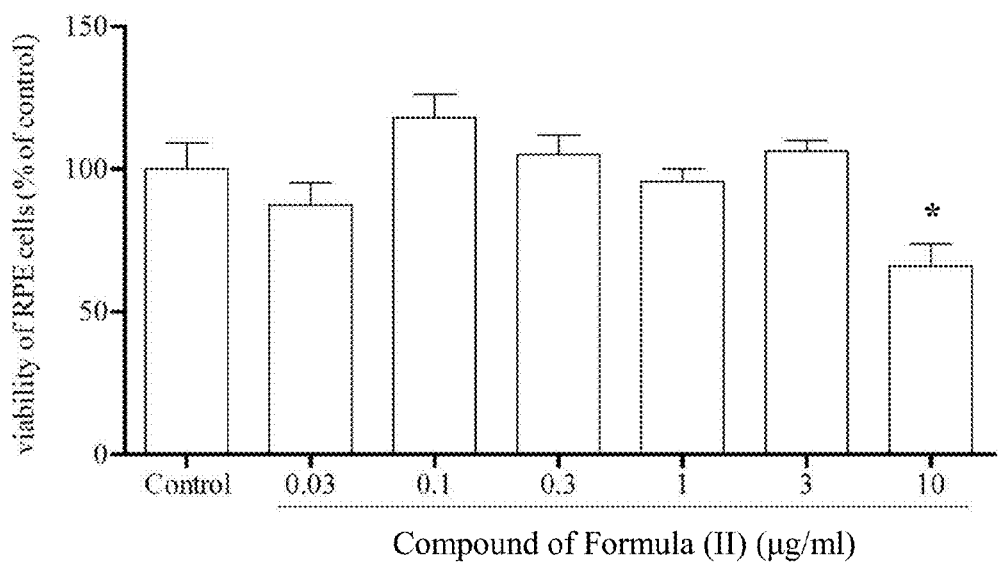
FIG. 1A shows the effect of a compound of Formula (II) on proliferation of ARPE-19 cells. ARPE-19 cells were incubated with the compound of Formula (II) ("(II)") for 72 hours.
Figure 1B:
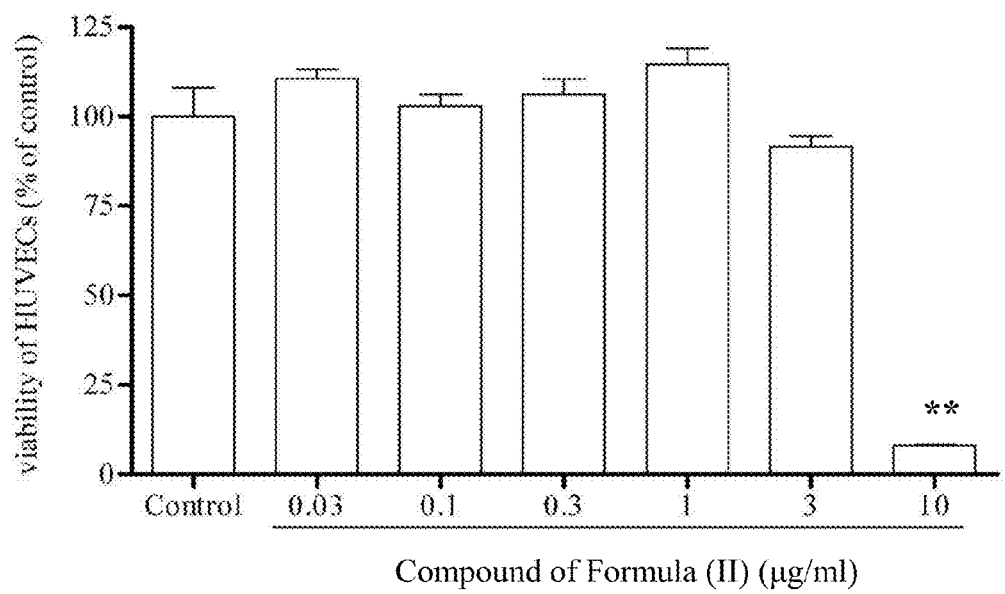
FIG. 1B shows the effect of (H) on proliferation of HUVECs. HUVECs were incubated with (II) for 72 hours. Data are expressed as means SEM. n=6 in each group; *P<0.05, **P<0.01 (II) group vs. vehicle control group.

The results showed that (II) did not affect the proliferation of ARPE-19 cells or HUVECs from 0.03 μg/ml to 3 μg/ml. However, (II) significantly inhibited the proliferation of ARPE-19 cells and HUVECs by 34% and 92% at the concentration of 10 µg/ml, respectively (FIGS. 1A and 1B). However, the former is much less than the latter.

Figure 2A:
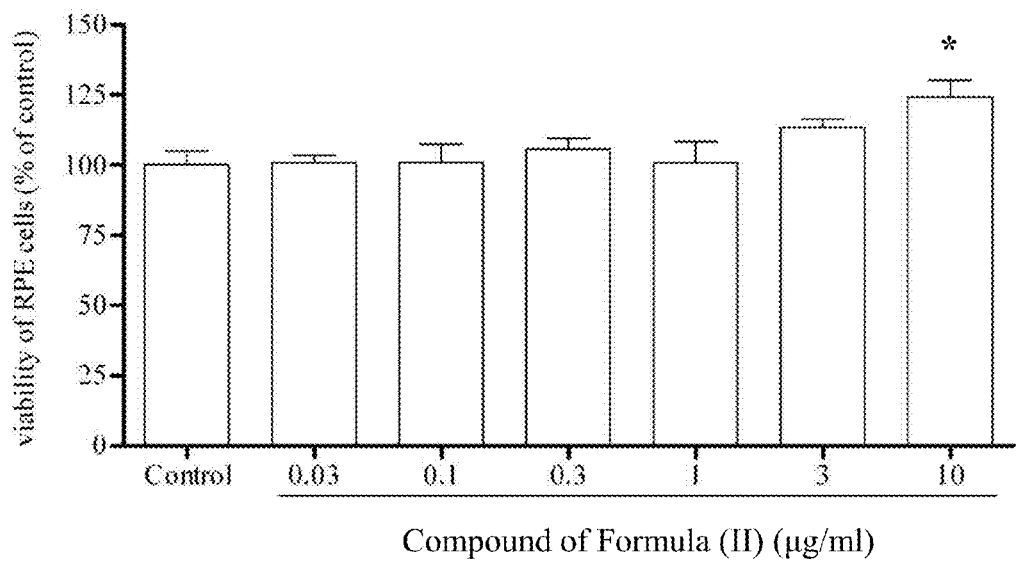
FIG. 2A shows the effect of (II) on hypoxia-induced injury in ARPE-19 cells. ARPE-19 cells were incubated with (II) for 72 hours.
Figure 2B:
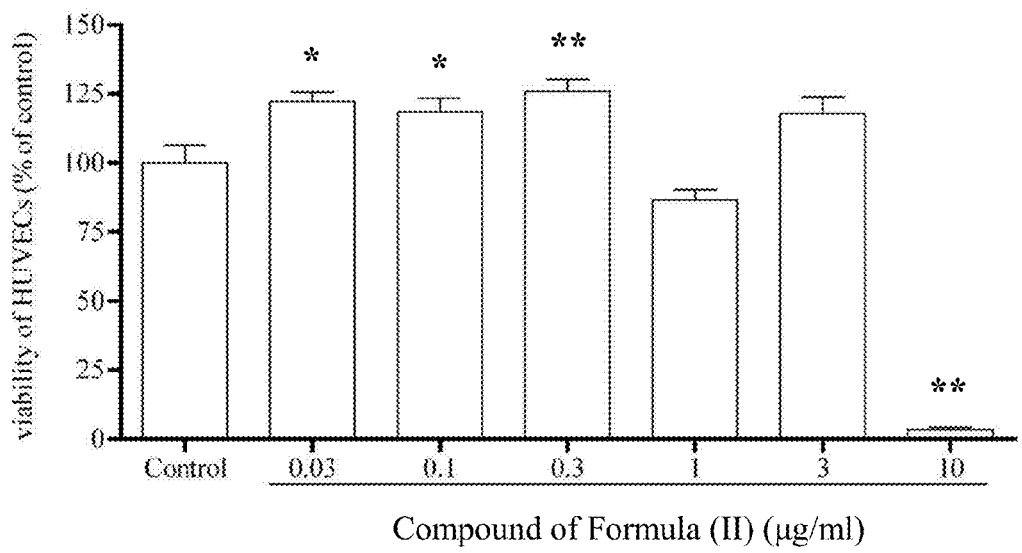
FIG. 2B shows the effect of (II) on hypoxia-induced injury in HUVECs. HUVECs were incubated with (II) for 72 h. Control group treated with vehicle (30% HP-β-CD solution) under normal condition (5% $CO_2$ and 95% air) for 72 hours; model group treated with vehicle under hypoxic condition (1% $O_2$, 5% $CO_2$ and 94% $N_2$) for 72 hours. Data are expressed as means±SEM. n=6 in each group; *P<0.05 and **P<0.01 vs. model group.

2. Effect of (II) on Hypoxia-Induced Damage in ARPE-19 Cells and HUVECs (II) had no effect on the viability of ARPE-19 cells in hypoxic condition from 0.03 dg/ml to 3 µg/ml (FIG. 2A). At the concentration of 10 µg/ml, (II) reversed the injury induced by hypoxia by 24% in ARPE-19 cells. Although (II) significantly increased the viability of HUVECs by 22%, 19% and 26% in hypoxic condition at concentration of 0.03, 0.1 and 0.3 µg/ml, respectively (FIG. 2B), yet at the concentration of 10 µg/ml, (II) significantly decreased the viability of HUVECs by 97% ($P<0.01$).

3. Effect of (II) on $NaIO_3$-Induced Injury in ARPE-19 Cells and HUVECs

Figure 3A:
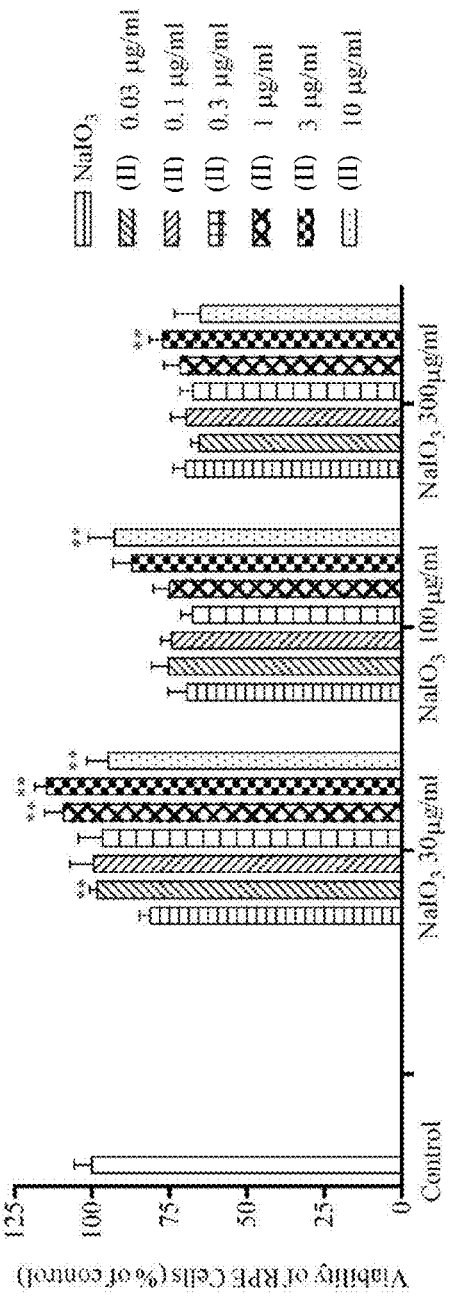
FIG. 3A shows the effect of (II) on $NaIO_3$-induced injury in ARPE-19 cells. ARPE-19 cells were incubated with (II) and $NaIO_3$ for 72 h.
Figure 3B:
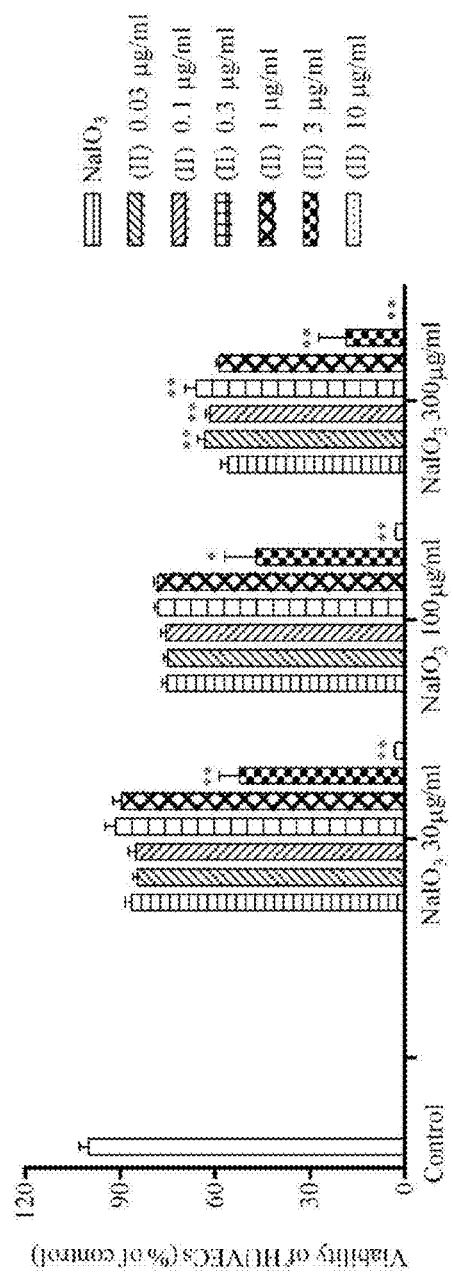
FIG. 3B shows the effect of (II) on $NaIO_3$-induced injury in HUVECs. HUVECs were incubated with (II) and $NaIO_3$ for 72 hours. Data are expressed as means±SEM. n=6 in each group; *P<0.05 and **P<0.01 vs. model group.

At the concentration of 0.03, 1, 3 and 10 µg/ml. (II) significantly reversed the viability of 30 µg/ml NaIO3-induced injury in ARPE-19 cells ($P<0.05$, FIG. 3A). (II) also reversed the viability of 100 and 300 µg/ml $NaIO_3$-induced injury by 24% and 7% in ARPE-19 cells at the concentration of 10 and 3 µg/ml, respectively ($P<0.05$, FIG. 3A). However, at the concentration of 3 and 10 µg/ml, (II) enhanced the $NaIO_3$-induced injury in HUVECs (FIG. 3B).

4. Effect of (II) on $H_2O_2$-Induced Injury in ARPE-19 Cells and HUVECs

At the concentration of 10 µg/ml, (II) reversed 200 µM and 400 µM $H_2O_2$-induced injury in ARPE-19 cells by 55% and 72%, respectively ($P<0.01$, FIG. 4A). On the other hand, 0.3 and 1 µg/ml (II) also reversed $H_2O_2$-induced injury in HUVECs. However, 10 µg/ml (II) enhanced 200 and 400 µM $H_2O_2$-induced injury by 63% and 42% in HUVECs, respectively ($P<0.01$, FIG. 4B).

5. Effect of (II) on $NaN_3$-Induced Injury in ARPE-19 Cells and HUVECs (II) significantly reversed NaN3-induced injury in ARPE-19 cells from 0.03 µg/ml to 10 µg/ml (FIG. 5A). At the concentration of 10 µg/ml, (II) enhanced 0.3, 1 and 3 mM NaN3-induced injury in HUVECs by 95%, 75% and 71%, respectively ($P<0.01$, FIG. 5B). 3 µg/ml (II) also enhanced 0.3 and 3 mM NaN3-induced injury in HUVECs by 75% and 44% (FIG. 5B).

6. Effect of (II) on t-BHP-Induced Injury in ARPE-19 Cells and HUVECs (II) significantly reversed t-BHP-induced injury in ARPE-19 cells (FIG. 6A). However, 10 µg/ml (II) enhanced 50, 100 and 200 µM t-BHP-induced injury in HUVECs by 71%, 80% and 76%, respectively ($P<0.01$, FIG. 6B). 3 µg/ml (II) also enhanced 50 and 100 µM t-BHP-induced injury in HUVECs by 27% and 21% (FIG. 6B).

Example 3

Enhancement of Ocular Blood Flow (OBF)

Ocular blood flow is closely related to numerous eye diseases, including glaucoma, ischemic retinopathy, diabetic retinopathy and age-related macular degeneration (AMD). Thus, maintenance of normal ocular blood flow is essential to prevent/treat the aforementioned eye diseases.

Materials and Methods

1. Materials 0.5% alcaine was purchased commercially. A 20% sterilized hypertonic saline solution was prepared in the laboratory. Colored microspheres were purchased from E-Z Trac (Los Angeles, Calif.). The colored microspheres were diluted with saline containing 0.01% (v/v) of Tween 80 to prevent the microspheres from sticking together. Two million microspheres in 0.4 ml were injected at each time point.

Female New Zealand white rabbits weighing 2.-3.0 kg, were purchased commercially. Animal care and treatment were followed by the institutional guidelines.

2. Methods

Rabbits were anesthetized with 35 mg/kg ketamine and 5 mg/kg xylazine by intramuscular injection. Half of the initial dose was given every one hour thereafter. The left ventricle was cannulated through the right carotid artery for injection of colored microspheres and the femoral artery was cannulated for collection of blood samples. The left eye was treated with one drop of proparacaine hydrochloride ophthalmic solution (Bausch & Lomb, Inc., Tampa, Fla., USA). The needle was inserted directly into the anterior chamber of the left eye, which was connected to the 40 mmHg saline manometer. The ocular hypertensive model reduced the ocular blood flow to approximately one third of the normal valued. 50 µl of 10 g/l flavone or vehicle (30% HP-β-CD solution) was instilled topically to the left eye 30 minutes after the ocular hypertensive model was built. The ocular blood flow was measured by colored microspheres at 0, 30, 60 and 120 minutes after treatment with the compounds or vehicle. At each time point, 2 million microspheres were injected as a reference, and blood samples were taken from the femoral artery for exactly one minute following injection of the microspheres. The blood sample was collected in a heparinized tube and the volume was recorded. The rabbits were euthanized with an injection of 100 mg/kg pentobarbital sodium after the last blood sampling. The left eyes were enucleated and dissected into the iris, ciliary body, retina and choroid. All the tissues were weighed.

The details of sample processing and microsphere counting were provided by E-Z Trac (Los Angeles, Calif., USA). In brief, the blood hemolysis reagent was added to the microfuge tubes with the blood sample, then vortexed and centrifuged for 30 minutes at 6000 rpm. The supernatant was removed, and then tissue/blood digest reagents I and II were added. The tubes were capped, vortexed, and centrifuged for 30 minutes. The supernatant was removed, and the counting reagent was added, vortexed, and centrifuged for 15 minutes. The supernatant was removed, and the microspheres were resuspended in a precise volume of the counting reagent. The number of microspheres was counted by the hemocytometer under the microscope. Tissue/blood digest reagent I was added to the microfuge tubes with the tissue samples, sealed, and heated at 95° C. for 15 minutes. Then the tubes were vortexed for 30 seconds, reheated, and revortexed until all tissue samples were dissolved. The tissue/blood digest reagent II was added while the tissue samples were still hot, then the tubes were capped, vortexed, and centrifuged for 30 minutes. The protocol thereafter was the same as that used to process the blood samples, and the microspheres were counted.

The blood flow of each tissue at a certain time point was calculated according to the following formula: Qm=(Cm×Qr)/Cr. Qm is the blood flow of a tissue in terms of µl/min/mg, Cm is the microsphere numbering of tissue, Qr is the flow rate of blood sample in terms of µl/min, and Cr is the microsphere number in the referenced blood sample.

Results

The blood flow in iris and choroid was significantly increased by 1% compound of Formula (I) ("(I)") and 1% (II) at 30 minutes after drug instillation (FIGS. 7A-7C and FIGS. 8A-8C, respectively).

Example 4

Facilitation of Retinal Function after Ischemic Insult

Measurement of intraocular pressure (IOP) alone should not be the sole determinant for a diagnosis of glaucoma, and reduction of IOP alone should not be the sole evaluant in new drug development (Chiou et al., Ophthalmic Res. 18:265-269, 1986). The ideal antiglaucoma agents should be able to lower the IOP and to improve the ocular blood flow as well (Hong et al., J. Ocular Pharmacol. 9:117-124, 1993). Studies on blood flow in various parts of the eye will not only lead to an understanding of the drugs mechanism of action but also to the development of a safer antiglaucoma drug (Chiou et al., Ophthalmic Res. 18:265-269, 1986). In addition, retinal degeneration is a leading cause of blindness, second only to glaucoma (Lierman, Mary Ann Liebert, Inc., New York, N.Y., 1987). The majority of retinopathy is caused by ischemic degeneration, which is difficult to treat even though numerous agents, including vasodilating agents, anticoagulants and blood viscosity reducing agents have been tried (O'Connor, Medcom, Inc., New York, N.Y., 1974). To date, none of these agents seems to benefit ischemic retinopathy (LaVail et al., Alan R. Liss, Inc., New York, N.Y., 1985.). Therefore, it is important to develop new agents which can be used to treat ischemic retinal degeneration. The recovery of retinal function after ischemia can be determined by the recovery of b-wave amplitude in electroretinography. In addition to glaucoma, AMD, DR and DME could also be benefited by these drugs which can facilitate retinal function recovery.

Materials and Methods

1. Methods

The retinal ischemia experiment has been described previously (Chiou et al., J. Ocular Pharmacol. 9:179-185, 1993, and Chiou et al., J. Ocular Pharmacol. 10:493-498, 1994). Electroretinograms (ERG) were carried out to assess the retinal function prior to and after the ischemic insult. ERGs were recorded using Ag/AgCl electrodes placed in contact with the cornea. One stainless steel needle was inserted subcutaneously between the two eyes as a reference electrode, and another needle was inserted subcutaneously into the neck as a ground electrode. A photostimulator (Grass PS22 Flash) was used to produce flashes of light 5 inches from the eye, and the ERG potentials were recorded on a polygraph. The ERG system was purchased from LKC Technologies, Inc. (Gaithersburg, Md.). A single flash (10 msec) of white light stimuli was used to evoke ERG a- and b-waves. Peak b-wave amplitudes were measured from the trough of the a-wave to the peak of the b-wave.

Long-Evans rats (200-250 g), dark-adapted at least 2 hours, were anaesthetized intramuscularly with ketamine (35 mg/kg) plus xylazine (5 mg/kg). Half of the initial dose was administrated at one hour intervals to maintain adequate anesthesia. The pupils were dilated with 1% tropicamide (50 µl) for ERG experiments. Retinal ischemia was produced by occlusion of the central retina and posterior ciliary arteries using a ligature placed around the optic nerve and posterior ciliary artery. The ligature was drawn tightly through a micropipette tip placed at the base of the eyeball socket to occlude the retinal vessels for 30 min. After 30 min of retinal ischemia, the ligature was liberated and the retinal arteries allowed to reperfuse. ERGs were measured at 30, 60, 90, 120, 180 and 240 min thereafter. The compounds and vehicle were administered topically before occlusion of the central retinal arteries.

2. Statistical Analysis

All data were expressed as mean±SEM. Student's t-test was used to analyze the significance of the results. The probability value (P) of <0.05 was considered to be significant in all experiments.

Results

When the central retina and posterior ciliary arteries were ligated, the blood flow to these arteries stopped and the b-wave of ERG dropped to zero quickly. When the ligation is removed, blood flow resumed as before yet the b-wave amplitude recovered to only 20% of the original level. When I % (I) was instilled, however, the h-wave amplitude-returned to approximately 50% of the original level (FIG. 9) and the drug action lasted at least 240 min after drug application.

Similar results were obtained with 1% (II) except the duration of drug action was shorter to last for only 120 min (FIG. 10). The potency, however, was about the same as 1% (I).

Example 5

Inhibition of Laser Induced AMD

Age-related macular degeneration (AMD) is the leading disease of visual impairment in western countries in patients over 50 years of age. The prevalence of AMD increases with age so that up to one third of individuals aged 75 and older suffered from some form of AMD. Given the enormous impact of AMD on the aging population, much public interest and research has been focused on this condition in the past decade.

AMD initially occurs in a "dry" form with pathological changes in the retinal pigment epithelium (RPE) and drusen formation, and can progress to geographic atrophy and/or "wet" form of AMD with choroidal neovascularization (CNV) (Klein, Ophthalmology 1997; 104:7-21). The breakdown of Bruch's membrane under the detached RPE serves as an entrance for new and immature choroidal vessels to grow into the subretinal space that leads to the formation of CNV. CNV can leak fluid as well as hemorrhage in the subretinal space resulting in blurry vision, visual distortion and sudden loss of vision. If left untreated, these lesions progress to form an organized fibrous scar, termed a disciform scar, which typically results in irreversible central vision loss.

Materials and Methods

The rats were randomly divided into 2 groups. Control group was instilled with vehicle (30% HP-β-CD solution). Experimental group was instilled with 5 mg/ml eye drops of a compound of the present invention. Both eyes of all rats were instilled with 1 drop of ophthalmic solutions 3 times a day for 1 week before and 4 weeks after laser induced injury. The rats were anesthetized for all procedures with intramuscular injection of ketamine (35 mg/kg) and xylazine (5 mg/kg). The pupils were dilated with one drop each of 10 mg/ml atropine, and 25 mg/ml phenylephrine. The fundus was visualized by the VOLK super Pupil XL Biomicroscopy Lens (Keeler Instruments Inc., Broomall, Pa., USA). A double frequency Nd:YAG laser (Laserex LP3532; Lumenis Inc., Salt Lake City, Utah, USA) was used at 532 nm wavelength. Laser parameters were used by 100 µm spot size, 0.15-second exposure and 150-200 mw powers. Five laser spots were made to the ocular fundus at approximately equal distances around the optic nerves. Acute vapor bubbles suggested rupture of Bruch's membrane. Only laser spots with bubble formation were included in the study. Lesions with subretinal hemorrhage were excluded. Fluorescein angiography (FA) was performed after 2 and 4 weeks laser treatment with a digital fundus camera (TRC-50EX; TOPCON, Tokyo, Japan). 100 mg/ml fluorescein sodium salt was injected (0.5 ml/kg) through hypoglossal vein. Both early (under 2 minutes) and late (over 7 minutes) fluorescein phases were captured. 100 mg/ml fluorescein isothiocyanate-dextran was injected (1.4 mg/kg) through hypoglossal vein after 3 drops of fluorescein sodium salt injection. Fluorescein pictures were taken within 20 minutes. The clearest pictures were chosen for the areas of CNV formation measurement by Imagenet2000 digital imaging system (Topcon Medical Systems, Inc., Paramus, N.J. USA).

Results

When Bruch's membrane of the rat eye was ruptured with laser beam, the fluorescein leakage was measured with fluorescein angiography. The area of CNV formation was measured quantitatively with computer and expressed in $mm^2$. As can be seen from FIG. 11, the control eye produced approximately 2.5 $mm^2$ CNV area which was significantly suppressed by 10% (II) instillation.

Example 6

Reduction of $NaIO_3$-Induced Dry AMD

A 2004 analysis reported that among Americans over the age of 40, AMD and/or geographic atrophy were present in at least one eye in 1.47% of the population, and that 1.75 million individuals have AMD. The prevalence of AMD increased dramatically with age, with more than 15% of the white women older than 80 years having neovascular AMD and/or geographic atrophy. More than 7 million individuals are at substantial risk of developing AMD. Owing to the rapidly aging population, the number of persons having AMD will increase by 50% to 2.95 million in 2020. In another study, AMD was reported to account for 54% of all current cases of blindness among the Caucasian population in the United States. The study predicted that the number of blind people in the US could increase by as much as 70% by 2020.

Materials and Methods

A total of thirty 8-week-old male Brown-Norway (BN) rats were randomly divided into 3 groups, 10 rats in normal group, 10 rats in $NaIO_3$ group and 10 rats in (II)+$NaIO_3$ group. Control group was instilled with solvent (2-hydroxypropyl-β-cyclodextrin, Sigma-Aldrich) alone without $NaIO_3$ injection. $NaIO_3$ group was instilled with solvent plus 35 mg/kg $NaIO_3$ injection through hypoglossal vein; whereas (II)+$NaIO_3$ group was instilled with 1% (II) eye drops plus 35 mg/kg $NaIO_3$ injection. Both eyes of all rats were instilled with 1 drop for 3 times a day for 1 week before and 4 weeks after $NaIO_3$ injection. At the end of 2 and 4 weeks, RPE function was measured with c-wave of ERG.

BN rats were dark adapted for 2 hours, and then anesthetized with ketamine 35 mg/kg plus xylazine 5 mg/kg i.m, Half of the initial dose was given each 1 hour thereafter. Pupils of all rats were dilated with one drop each of 1% atropine, and 2.5% phenylephrine. Before recording, one drop of 0.5% tetracaine was given for surface anesthesia. All rats were kept warm during ERG measurement. DC-ERG recording methods developed by Peachey were followed. Briefly, a 1-mm diameter glass capillary tube with filament (Sutter Instruments, Novato, Calif.) that was filled with Hanks balanced salt solution (Invitrogen, Carlsbad, Calif.) was used to connect with an Ag/AgCl wire electrode with an attached connector. The electrode was positioned to the corneal surface. Responses were amplified (dc-100 Hz; gain=1000X; DP-31, Warner Instruments, Hamden, Conn.) and digitized at 10 Hz or 1000 Hz. Data were analyzed by iWORX LabScribe Data Recording Software (iWorxOCB Sciences, Dover, N.H.).

Light stimuli was derived from an optical channel using a fiber-lite high intensity illuminator (Dolan-Jenner Industries, Inc. MA), with neutral density filters (Oriel, Stratford, Conn.) placed in the light path to adjust stimulus luminance. The stimulus luminance used in this experiment was 3.22 log $cd/m^2$ and stimulated for 4 minutes. Luminance calibration was made by a Minolta (Ramsey, N.J.) LS-110 photometer focused on the output side of the fiber optic bundle where the rat eye was located.

Results

When rats were treated with $NaIO_3$, it caused degeneration of RPE cells specifically. As a result, $NaIO_3$ was used to develop dry AMD animal model and the damaged cell function was measured with c-wave amplitude of ERG. As can be seen from FIG. 12, the control c-wave of ERG was markedly suppressed by $NaIO_3$. However, treatment of $NaIO_3$-treated rats with 1% (II) can markedly reverse its c-wave of ERG. $NaIO_3$ is a potent toxin to degenerate RPE cells specifically in the eye. As a result, the c-wave of ERG suppressed almost completely in the $NaIO_3$-treated eye (FIG. 12). It is important to note that this $NaIO_3$ induced dry AMD model can be reversed 4 times by 1% (II) (FIG. 12). If the $NaIO_3$ suppression was minimized somewhat by giving smaller dose, the reversal by 1% (II) could be more apparent and impressive. Since dry AMD is a dreadful disease to cause blindness, any drugs which can prevent/treat. dry AMD are very valuable.

It will be appreciated by those skilled in the art that changes could be made to the embodiments described above without departing from the broad inventive concept thereof. It is understood, therefore, that this invention is not limited to the particular embodiments disclosed, but intended to cover modifications within the spirit and scope of the present invention as defined by the appended claims.

What is claimed is:

1. A method for treating an ocular disease other than an eye cancer in a subject in need thereof, comprising administering to the subject a pharmaceutical composition comprising an effective amount of a compound selected from the group consisting of:

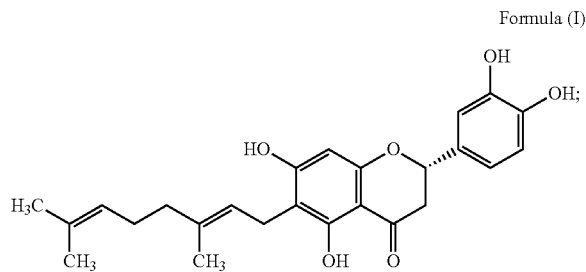 [SMILES: CC(C)=CCC/C(C)=C/Cc1c(O)cc2c(c1O)C(=O)C[C@@H](c1ccc(O)c(O)c1)O2]

Formula (I)

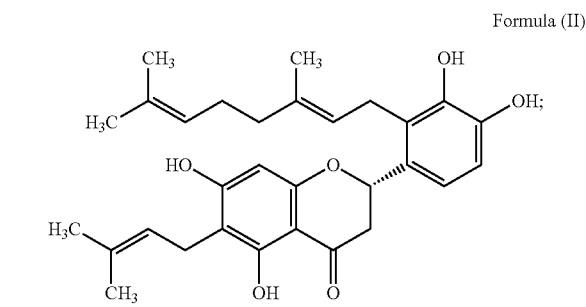 [SMILES: CC(C)=CCC/C(C)=C/Cc1c([C@@H]2CC(=O)c3c(cc(O)c(CC=C(C)C)c3O)O2)ccc(O)c1O]

Formula (II)

Formula (III)
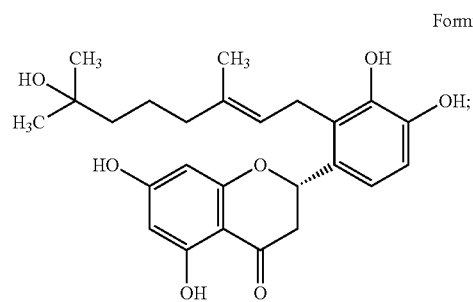
Formula (IV)
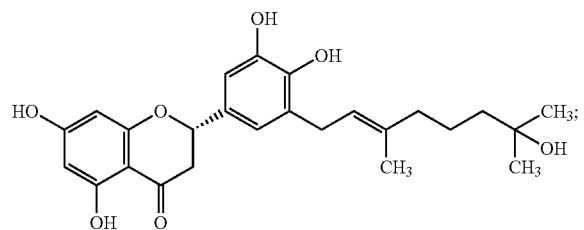
Formula (V)
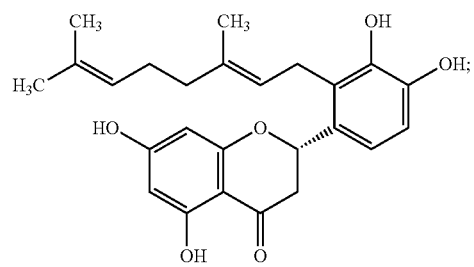
Formula (VI)
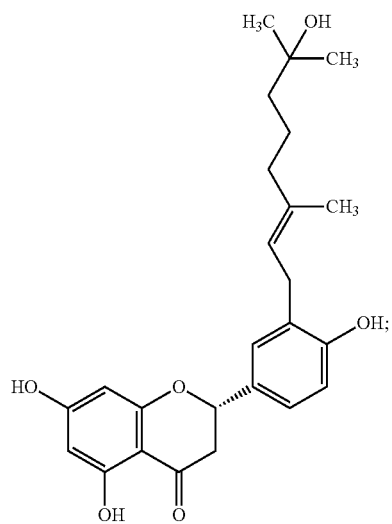
Formula (VII)
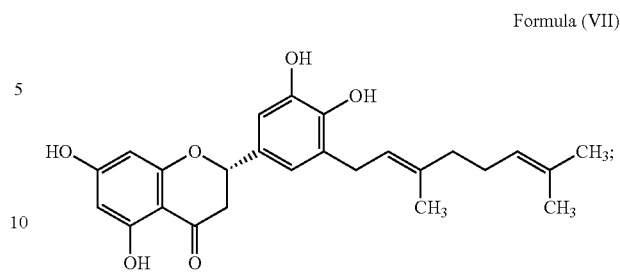
Formula (VIII)
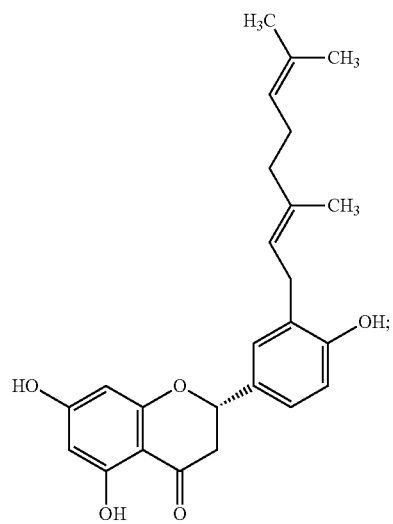
Formula (IX)
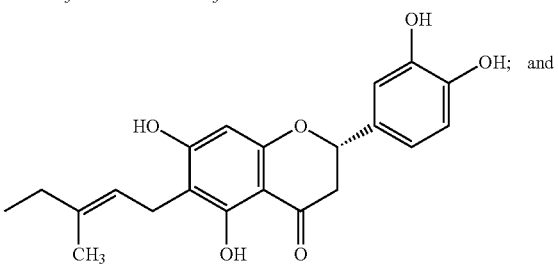
and
Formula (X)
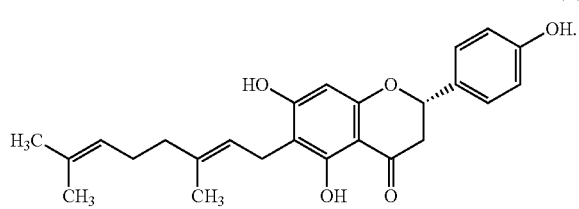

2. The method of claim 1, wherein the effective amount is an amount selected from the group consisting of: an amount effective to enhance the viability of RPE cells suffering from oxidative stress and/or hypoxia-induced damages; an amount effective to enhance the viability of RPE cells suffering from oxidative stress and/or hypoxia-induced damages, and in the same time having little or no effect on the viability of human umbilical vein endothelial cells (HUVECs) or effective to decrease the viability of HUVECs; an amount effective to enhance ocular blood flow; an amount effective to reduce choroidal neovascularization (CNV); an amount effective to enhance RPE function; and an amount effective in achieving a combination of the above-mentioned efficacies.

3. The method of claim 1, wherein the ocular disease is selected from the group consisting of glaucoma, age-related macular degeneration (AMD), ischemic retinopathy, optic neuropathy, diabetic retinopathy, diabetic macular edema, uveitis, and senile cataract.

4. The method of claim 3, wherein the ocular disease is AMD.

5. The method of claim 4, wherein the AMD is dry AMD.

6. The method of claim 1, wherein the pharmaceutical composition is administered to the subject topically in the eyes or orally.

7. The method of claim 1, wherein the pharmaceutical composition is in the form of eye ointment, eye gel, eye cream, or eye drops.

* * * * *